United States Patent [19]

Clemence et al.

[11] Patent Number: 4,877,796
[45] Date of Patent: Oct. 31, 1989

[54] DECAHYDROQUINOLINES AND CENTRAL ANALGESIC METHOD OF USE THEREOF

[75] Inventors: François Clemence; Odile Le Martret, both of Paris; Françoise Delevallee, Fontenay Sous Bois; Michel Fortin, Paris, all of France

[73] Assignee: Roussel Uclaf, Paris, France

[21] Appl. No.: 84,456

[22] Filed: Aug. 12, 1987

[30] Foreign Application Priority Data

Aug. 12, 1986 [FR] France .................................. 86 11620
Jul. 9, 1987 [FR] France .................................. 87 09747

[51] Int. Cl.⁴ ..................... C07D 215/40; A61K 31/47
[52] U.S. Cl. .................................... 514/311; 546/164; 546/165
[58] Field of Search ........................ 546/164; 514/311

[56] References Cited

U.S. PATENT DOCUMENTS 4,480,099 10/1984 Hadley ............................. 546/164

FOREIGN PATENT DOCUMENTS 7732621 6/1978 France .

OTHER PUBLICATIONS

Szmuszkovicz et al. "Benzeneacetamide Amines", J. Med. Chem., 25, pp. 1125-1126, (1982).

Primary Examiner—David B. Springer
Attorney, Agent, or Firm—Bierman and Muserlian

[57] ABSTRACT

A compound selected from the group consisting of all enantiomeric and diastereoisomeric forms of a decahydroquinoline of the formula

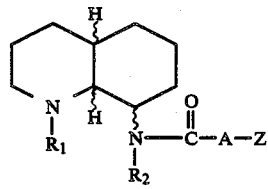

wherein $R_1$ is alkyl of 1 to 5 carbon atoms, $R_2$ is selected from the group consisting of hydrogen and akyl of 1 to 5 carbon atoms, A is selected from the group consisting of $-(CH_2)_n-$, $-CH_2O-$ and alkylene substituted with alkyl having a total of 2 to 8 carbon atoms, n is an integer from 0 to 5, Z is selected from the group consisting of optionally substituted phenyl, optionally substituted naphthyl, optionally substituted indenyl, optionally substituted heteromonocycle of 5 to 6 members and optionally substituted heterobicycle with the proviso that when Z is o-alkoxy-phenyl, A is not $-(CH_2)_n-$ in which n is O, and their non-toxic, pharmaceutically acceptable acid addition salts and their quaternary ammonium salts and intermediates having analgesic, diuretic, hypotensive, anti-arrithmic and anti-cerebral-ischaemic properties.

18 Claims, No Drawings

DECAHYDROQUINOLINES AND CENTRAL ANALGESIC METHOD OF USE THEREOF

STATE OF THE ART

Related prior art are Journal of Med. Chem., Vol. 25, October 1982, p. 1125-1126 and Vol. 17, November 1974, p. 1136-1139 and copending U.S. patent application Ser. No. 002,778 filed Jan. 13, 1987, U.S. Pat. No. 4,816,465, issued Mar. 28, 89.

OBJECTS OF THE INVENTION

It is an object of the invention to provide the novel compounds of formula I and their non-toxic, pharmaceutically acceptable acid addition salts and quaternary ammonium salts and a process and intermediates for their preparation.

It is another object of the invention to provide novel central analgesic compositions and a novel method of inducing central analgesic activity in warm-blooded animals.

These and other objects and advantages of the invention will become obvious from the following detailed description.

THE INVENTION

The novel compounds of the invention are selected from the group consisting of all enantiomeric and diastereomeric forms of a decahydroquinoline of the formula

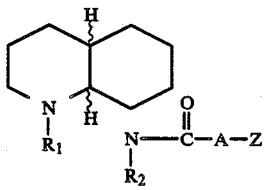

wherein $R_1$ is alkyl of 1 to 5 carbon atoms, $R_2$ is selected from the group consisting of hydrogen and alkyl of 1 to 5 carbon atoms, A is selected from the group consisting of $-(CH_2)_n-$, $-CH_2O-$ and alkylene substituted with alkyl having a total of 2 to 8 carbon atoms, n is an integer from 0 to 5, Z is selected from the group consisting of optionally substituted phenyl, optionally substituted naphthyl, optionally substituted indenyl, optionally substituted heteromonocycle of 5 to 6 members and optionally substituted heterobicycle with the proviso that when Z is o-alkoxy-phenyl, A is not $-(CH_2)_n-$ in which n is 0, and their non-toxic, pharmaceutically acceptable acid addition salts and their quaternary ammonium salts.

Examples of substituents when Z is phenyl are alkyl and alkoxy of 1 to 5 carbon atoms, halogen, $-OH$, $-CF_3$, $-NO_2$, $-NH_2$ and mono and dialkylamino of 1 to 5 alkyl carbon atoms. Examples of substituents when Z is naphthyl, indenyl or heterocycle are alkyl and alkoxy of 1 to 5 carbon atoms, $-CF_3$, $-NO_2$, $-NH_2$ mono- and dialkylamino of 1 to 5 alkyl carbon atoms and phenyl optionally substituted with one or more members of the group consisting of alkyl and alkoxy of 1 to 5 carbon atoms and halogen.

Examples of alkyl and alkoxy of 1 to 5 carbon atoms are methyl, ethyl, isopropyl, n-propyl, butyl, methoxy, ethoxy, isopropoxy, n-propoxy and butoxy. Examples of halogen are fluorine, bromine, chlorine and iodine. The mono- and dialkylamino preferably have methyl or ethyl as the alkyl.

Examples of Z as a heteromonocycle of 5 to 6 members are thiazolyl, pyridinyl, oxazolyl, isoxazolyl, imidazolyl and thienyl and examples of Z as a heterobicycle are indolyl, quinolyl, benzo[b]thienyl, benzimidazolyl, benzoxazolyl and benzothiazolyl.

When A is $-(CH_2)_n-$, n is preferably 0 or 1. When A is alkylene substituted by alkyl, the alkyl is preferably methyl or ethyl and specific examples are 1,1-ethanediyl, 1-methyl-1,2-ethanediyl, 1-methyl-1,3-propanediyl, 2-methyl-1,3-propanediyl and 1-ethyl-1,2-ethanediyl.

The compounds of formula I can exist in the form of four racemates or pairs of enantiomers which pairs can be separated by known procedures. The invention relates to all enantiomeric and diastereoisomeric forms.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid and aspartic acid, alkane sulfonic acids such as methane sulfonic acid, arylsulfonic acids such as benzene sulfonic acid and arylcarboxylic acids such as benzoic acid.

Examples of quaternary ammonium salts are the compounds of formula I quaternized with an R—Y compound in which R is alkyl of 1 to 4 carbon atoms such as methyl, ethyl, isopropyl and n-propyl and Y is a halide such as chloride, bromide or iodide.

Among the preferred compounds of formula I are those wherein $R_1$ is alkyl of 1 to 5 carbon atoms, A is a linear $-(CH_2)_n-$, n is a whole number from 0 to 5 or a branched alkylene of 2 to 8 carbon atoms, $R_2$ is hydrogen or alkyl of 1 to 5 carbon atoms, Z is phenyl substituted by X and X' which are individually hydrogen, alkyl and alkoxy of 1 to 4 carbon atoms, $-OH$, halogen, $-CF_3$, $-NO_2$, $-NH_2$ and mono- and dialkylamino with the proviso that when X or X' is o-alkoxy on the phenyl and A is $-(CH_2)_n-$, n is not 0 and their acid addition and quaternary ammonium salts in all possible enantiomeric and diastereoisomeric forms.

The preferred compounds of formula I are those wherein the junction of the rings is cis and those wherein A is $-CH_2-$ or $-CH_2O-$ and their non-toxic, pharmaceutically acceptable acid addition salts.

A particular preferred group of compounds are those wherein $R_1$ is methyl or ethyl, $R_2$ is hydrogen, methyl or ethyl and Z is phenyl optionally substituted with 1 or 2 members of the group consisting of methyl, ethyl, methoxy, ethoxy, chlorine, bromine, $-CF_3$ and $-NO_2$ and those wherein $R_1$ is methyl or ethyl, $R_2$ is hydrogen, methyl or ethyl and Z is naphthyl, pyridinyl or benzo[b]thienyl and their non-toxic, pharmaceutically acceptable acid addition salts.

Specific preferred compounds of the invention are [4aRS(4aα,8α,8aα,)] (±) N-(decahydro-1-methyl-8-quinolinyl)-3,4-dichloro-N-methyl-benzene-acetamide and (4aα,8α,8aα) (±) N-(decahydro-1-methyl-8-quinolinyl)-[2-(3,4-dichlorophenoxy)]N-methyl-acetamide and their non-toxic, pharmaceutically acceptable acid addition salts.

The novel process of the invention for the preparation of compounds of formula I comprises reacting 8-chloro-5,6,7,8-tetrahydroquinoline with a compound of the formula X—$R_1$ wherein $R_1$ is alkyl of 1 to 5 carbon atoms and X is halogen to obtain a compound of the formula

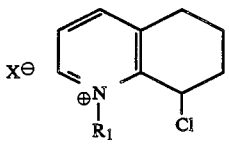

reacting the latter with an amine of the formula $R_2$—$NH_2$ wherein $R_2$ is hydrogen or alkyl of 1 to 5 carbon atoms to obtain a compound of the formula

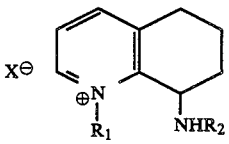

reducing the latter to obtain a product of the formula in all the possible enantiomeric and diastereoisomeric forms:

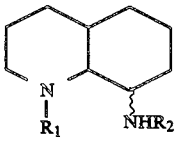

and condensing the latter with an acid of the formula or a functional derivative thereof:

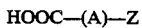

HOOC—(A)—Z                    V

A and Z have the above definitions to obtain a product of formula I in all the possible enantiomeric and diastereoisomeric forms, which can be resolved to obtain the optically active forms and which are treated if desired, with a mineral or organic acid to form the acid addition salts.

Preferably, X—$R_1$ is an alkyl halide and the reaction is effected in acetonitrile. The reduction of the compounds of formula III is effected by catalytic hydrogenation in the presence of platinum oxide. The carboxyl group of the compound of formula V is activated in the presence of carbonyldiimidazole or dicyclohexylcarbodiimide and the compound of formula V is preferably the acid chloride or mixed anhydride.

The two isomers of the compounds of formula IV have the —NH—$R_2$ group in the α- or β-orientation with respect to the ring and can be separated by chromatography. The racemates may be separated as salts of the diastereoisomers with optically active acids.

The compounds with the formula (I) as defined above as well as their addition salts with acids show useful pharmacological properties. They show in particular a strong affinity for the opiate receptors and in particular for the K receptors and are endowed with central analgesic properties.

They ae also endowed with diuretic properties, and anti-arrythmic anti-cerebral-ischaemic and hypotensive properties.

The subject matter of the invention is also the novel central analgesic composition which comprised at least one compound of formula I and its non-toxic, pharmaceutically acceptable acid addition salts and quaternary ammonium salts and an inert pharmaceutical carrier or excipient.

The compositions are useful for alleviating pain of any origin such as muscular, articular or nevous nature.

They can be used in the treatment of dental pains or migraines, shingles, in the treatment of severe pains, in particular those refractory to peripheral antalgesics, for example during néoplastic process, in the treatment of pancreatitis, renal or biliary colic, in the treatment of post-operation and post-traumatic pains.

The subject matter of the invention is also the novel diuretic compositions which comprise at least one compound of formula I and its non-toxic pharmaceutically acceptable acid and addition salts and quaternary ammonium salts and an inert pharmaceutical carrier or excipient.

The compositions can be used in the treatment of oedemato syndromes, of cardiac insufficiency, of certain obesities, of cirrhoses, in the treatment of severe refractory oedemas, in particular those of congestive cardiac insufficiency and in the lengthy treatment of arterial hypertension.

The subject matter of the invention is also the novel antiarrythmic compositions which comprise at least one compound of formula I and its non-toxi pharmaceutically acceptable acid addition salts and quaternary ammonium salts and an inert pharmaceutical carrier or excipient.

The compositions can be used in the treatment of ventricular, supraventricular and functional arrythmias. The compositions may be in the form of tablets, dragees, gelules, granules, suppositories, creams, ointments, gels, aerosols and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The novel method of relieving pain in warm-blooded animals including humans, comprises administering to warm-blooded animals a central analgesically effective amount of at least one compound of formula I and its non-toxic, pharmaceutically acceptable acid addition salts and quaternary ammonium salts. The compounds may be administered orally, rectally or parenterally and the usual daily dose is 0.05 to 6 mg/kg depending on the condition treated, the specific compound and method of administration. For example, a daily oral dose of 0.2 to 6 mg/kg is useful for analgesic activity.

The novel method of inducing diuresis in warm-blooded animals a diuretically effective amount of at least one compound of formula I and its non-toxic, pharmaceutically acceptable acid addition salts and quaternary ammonium salts. The compound may be administered orally rectally or parenterally and the usual daily dose is $1\gamma$ to 1 mg/kg depending on the condition treated, the specific compound and method of administration. For example a daily oral dose of $\Lambda o\gamma$ to 1 mg and a daily parenteral dose of $1\gamma$ to $100\gamma$ kg are useful for diuretic activity, more particularly a daily oral dose of $10\gamma$ to $100\gamma/kg$ and a daily parenteral dose of $5\gamma$ to $50\gamma/kg$.

The novel method of treating arrythmia in warm blooded animals including humans, comprises administering to warm blooded animals a antiarythmically effective amount of at least one compound of formula I and its non-toxic, pharmaceutically acceptable acid addition salts and quaternary ammonium salts. The compounds may be administered preferably orally, rectally or parenterally and the usual daily dose is 3 to 12 mg/kg depending on the condition treated, the specific compound and method of administration.

The compounds of formulae III and IV are novel intermediates and 8-chloro-5,6,7,8-tetrahydroquinoline starting material may be obtained by the process of U.S. Pat. No. 3,991,065 by chlorination of 5,6,7,8-tetrahydroquinoline-N-oxide.

In the following examples there are described several preferred embodiments to illustrate the invention. However, it is to be understood that the invention is not intended to be limited to the specific embodiments.

EXAMPLE 1

[4aRS(4aα,8α,8aα)](±) N-(decahydro-1-methyl-8-quinolinyl)-3,4-dichloro-N-methyl-benzene-acetamide

STEP A:
8-iodo-1-methyl-5,6,7,8-tetrahydro-1-quinolinim iodide

A solution of 13.70 g of 5,6,7,8-tetrahydro-8-chloroquinoline (preparation given below), 86 ml of acetonitrile and 15.2 ml of methyl iodide was stirred for 68 hours at ambient temperature and crystallization was started after 50 minutes of reaction. The crystals were separated, rinsed with acetonitrile, then with ether and dried under reduced pressure at 20° C. to obtain 29.96 g of 8-iodo-1-methyl-5,6,7,8-tetrahydro-1-quinolinium iodide melting at 175° C.

Preparation of 5,6,7,8-tetrahydro-8-chloroquinoline 3 ml of methane sulfonyl chloride were slowly added at ambient temperature to 1.49 g of 5,6,7,8-tetrahydroquinoline N-oxide with stirring under an inert atmosphere and the mixture was then heated for 4 hours at 80°–82° C. and then cooled to 20° C. The mixture was poured into 20 ml of a saturated solution of sodium bicarbonate and then sodium bicarbonate was added slowly until an akaline pH was iobtained. Extraction was carried out with methylene chloride and the extracts were washed with water. The combined organic solutions were dried and distilled to dryness to obtain 1.53 g of 8-iodo-1-methyl-5,6,7,8-tetrahydro-1-quinolinium iodide in the form of an oil.

STEP B:
1-methyl-8-(methylamino)-5,6,7,8-tetrahydro-1-quinolinium iodide 8.02 g of the product of step A were introduced into 40 ml of tetrahydrofuran and then 7.4 ml of an ethanol solution of monoethylamine was added all at once with a pipette. The suspension was stirred for 20 hours at ambient temperature and the crystals were separated, rinsed with tetrahydrofuran and ether and dried under reduced pressure at 20° C. to obtain 4.76 g of 1-methyl-8-(methylamino)-5,6,7,8-tetrahydro-1-quinolinium iodide melting at 180° C.

STEP C: [4aRS(4aα,8α,8aα](±) decahydro-N,1-dimethyl-8-quinolinamine and [4aRS(4aα,8α,8aα)](±) decahydro-N,1-dimethyl-8-quinolinamine 1.029 g of platinum oxide were added all at once to a solution of 10.29 g of the product of Step B in 150 ml of acetic acid and the suspension was hydrogenated at 22° to 24° C. for 50 hours. After 29 hours of hydrogenation, 1 g more of platinum oxide was added and at the end of the reaction, 30 ml of water were added. After filtering, rinsing with methanol and distilling under reduced pressure, the residue was taken up in 200 ml of ether. 200 ml of sodium hydroxide solution diluted to one half were added slowly with stirring and cooling. After stirring and decanting, the aqueous phase was extracted with ether and the organic phases were dried and distilled under reduced pressure to obtain 5.60 g of [4aRS(4aα,8α,8aα,](±) decahydro-N,1-dimethyl-8-quinolinamine and [4aRS(4aα,8α,8aα,)](±) decahydro-N,1-dimethyl-8-quinolinamine which was a mixture of the 2 diastereoisomers at the junction of the cis ring.

Separation of the 2 diastereoisomers by preparative chromatography

A preparative chromatography was carried out on silica (eluent: ethyl acetate-methanol-triethylamine 85-10-5) at atmospheric pressure. it was left in contact with the eluent for one hour and 5.5 g of crude base were chromatographed. A fraction of 579 mg of a mixture of 3 mobile products was recovered first and then the fractions corresponding to the isomer having 8α-orientation were brought to dryness under reduced pressure. 1.122 g of product with 8α-orientation were obtained. The fractions corresponding to the isomer having 8β-orientation were brought to dryness under reduced pressure. 3.361 g of product with 8β-orientation were obtained.

STEP D: [4aRS(4aα,8α,8aα)](±) N-(decahydro-1-methyl-8-quinolinyl)-3,4-dichloro-N-methyl-benzene-acetamide and its hydrochloride 2.13 g of 3,4-dichlorophenyl acetic acid, 1.69 g of carbonyldiimidazole and 20 ml of tetrahydrofuran were stirred at 20° C. for 1 hour and then 1.46 g of 8α-diastereoisomer obtained in Step C in solution in 5 ml of tetrahydrofuran were added with stirring for 3 hours and 30 minutes at 20° to 22° C. The tetrahydrofuran was eliminated under reduced pressure and the residue was taken up by 50 ml of ether, washed with a saturated solution of sodium bicarbonate, then with salted water, dried, rinsed and concentrated under reduced pressure to obtain 3.73 g of crude product. The latter was purified by passage through poxalate and 3.645 g of crude product were dissolved in 10 ml of ethanol. 1.5 g of oxalic acid in solution in 2.5 ml of ethanol were added and the insoluble product was filtered off, rinsed with ethanol and dried under reduced pressure at 20° C. to obtain 464 mg of product. 120 ml of ether were added slowly to the mother liquors and a gum precipitated. The supernatant solution was decanted and rinsed with ether and the gum was taken up in water and made alkaline with sodium bicarbonate in the pressure of 50 ml of ether. After decanting, washing with salted water, drying and concentrating to dryness under reduced pressure, 2.29 g of [4aRS 4α,8α,8aα)](±) N-(decahydro-1-methyl-8-quinolinyl)-3,4-dichloro-N-methyl-benzene-acetamide were obtained in the form of an oily dry extract which crystallized and melting at 92° C.

Preparation of the hydrochloride 2.15 g of dry extract were dissolved in 5 ml of ethanol at 50° to 60° C. and after filtering, the filtrate was rinsed with ethanol and with ether. 2 ml of hydrochloric acid in ethanol were added and crystallization was started. A thick mass formed which was diluted with ether, separated, rinsed with ethanol, with an ether ethanol mixture (3–2) and then with ether. Drying under reduced pressure at 70° C. yielded 2.05 g of [4aRS 4α,8α,8aα)](±) N-(decahydro-1-methyl-8-quinolinyl)-3,4-dichloro-N-methyl-benzene-acetamide hydrochloride melting at 253° C.

EXAMPLE 2

[4aRS(4aα,8α,8aα)](+) N-(decahydro-1-methyl-8-quinolinyl)-3,4-dichloro-N-methyl-benzene-acetamide 1.46 g of dicyclohexylcarbodiimide were introduced into a solution of 1.46 g of 3,4-dichlorophenylacetic acid, 1.222 g of 8β-diastereoisomer obtained in Step C of Example 1 and 20 ml of methylene chloride and the mixture was stirred for 3 hours and 30 minutes, then filtered and rinsed with methylene chloride. The filtrate was concentrated to dryness under reduced pressure and the residue was taken up in ether, washed with a saturated aqueous solution of sodium bicarbonate, then with salted water, dried and concentrated to dryness under reduced pressure to obtain 2.845 g of product. The latter was taken up in 15 ml of ether and crystallization was started. The crystals were dried, rinsed with ether and dried under reduced pressure to obtain 2.053 g of product. 1.885 g of the product was purified by chromatography on silica (eluent: ethyl acetate with 2% of triethylamine) and the homogeneous fraction was evaporated to dryness to obtain 1.477 g of product which were dissolved in methylene chloride and filtered. The methylene chloride was distilled off under reduced pressure while introducing isopropyl ether. The product crystallized during distillation and the crystals were separated, rinsed with isopropyl ether, dried under reduced pressure at 50° C. to obtain 1.27 g of [4aRS(4aα,8α,8aα)](±) N-(decahydro-1-methyl-8-quinolinyl)-3,4-dichloro-N-methyl-benzene-acetamide melting at 139° C.

Preparation of the hydrochloride 1.2 g of the product were dissolved in 4.8 ml of ethanol and 1 ml of ethanol containing hydrochloric acid (5.75N) at 20° C. The solution was filtered and the filtrate was rinsed with ethanol and concentrated to dryness under reduced pressure. The residue was triturated in 10 ml of ether, separatedl, rinsed with ether and dried under reduced pressure at 70° C. to obtain 1.259 g of the hydrochloride melting at 258° C.

Using the procedure of Example 1, [4aRS(4aα,8α,8aα)](±) decahydro-N,1-dimethyl-8-quinolinamine and a suitable acid were reacted to obtain the products of Examples 3 to 11.

Example 3: [4aα,8α,8aα,](±) N-(decahydro-1-methyl-8-quinolinyl)-N-methyl-4-nitrobenzene-acetamide and its hydrochloride.

Example 4: [4aα,8α,8aα](±) N-(decahydro-1-methyl-8-quinolinyl)-N-methyl-4-(trifluoromethyl)-benzene-acetamide and its E-butene dioate.

Example 5: [4aα,8α,8aα] 4-bromo-N-(decahydro-1-methyl-8-quinolinyl)-N-methyl-benzene-acetamide and its hydrochloride.

Example 6: [4aα,8α,8aα](±) N-(decahydro-1-methyl-8-quinolinyl)-4,N-dimethyl-benzene-acetamide and its hydrochloride.

Example 7: [4aα,8α,8aα](±) N-(decahydro-1-methyl-8-quinolinyl)-2-(3,4-dichlorophenoxy)-N-methylacetamide and its E-butene dioate.

Example 8: [4aα,8α,8aα](±) N-(decahydro-1-methyl-8-quinolinyl)-3,4-dimethoxy-N-methyl-benzene-acetamide and its E-butene dioate.

Example 9: [4aα,8α,8aα](±) N-(decahydro-1-methyl-8-quinolinyl)-N-methyl-1-naphthalene-acetamide and its E-butene dioate.

Example 10: [4aα,8α,8aα](±) N-(decahydro-1-methyl-8-quinolinyl)-N-methyl-4-pyridine-acetamide and its oxalate Example 11: [4aα,8α,8aα](±) N-(decahydro-1-methyl-8-quinolinyl)-N-methyl-benzo(b)thiophene-acetamide.

The acid used, the results of the analysis and the melting points of the products obtained appear in Table I hereafter.

TABLE I

| Example | Acid used at the start | Microanalysis: Calculated/Found | | | | | | M.P. (°C.) |
|---|---|---|---|---|---|---|---|---|
| | | C % | H % | N % | Cl % | Br % | S % | |
| 3 | p-nitrophenyl acetic acid | 59.75 | 7.39 | 11.00 | 9.28 | | | #228 |
| | | 59.6 | 7.3 | 10.8 | 9.4 | | | (decomp) |
| 4 | p-trifuoromethyl acetic acid | 59.49 | 6.45 | 5.78 | 11.76 | | | 180 |
| | | 59.7 | 6.77 | 5.7 | 11.45 | | | |
| 5 | p-bromophenyl acetic acid | 54.88 | 6.79 | 6.74 | 8.52 | 19.22 | | >260 |
| | | 54.6 | 6.9 | 6.5 | 8.2 | 19.0 | | |
| 6 | p-tolyl acetic acid | 68.45 | 8.90 | 7.98 | 10.10 | | | >260 |
| | | 68.4 | 9.2 | 7.8 | 10.3 | | | |
| 7 | 3,4-dichlorophenoxy acetic acid | 55.09 | 6.03 | 5.59 | 14.14 | | | 205 |
| | | 55.1 | 6.1 | 5.5 | 14.0 | | | |
| 8 | 3,4-dimethoxyphenyl acetic acid | 63.01 | 7.61 | 5.88 | | | | #150 |
| | | 63.1 | 7.7 | 5.6 | | | | (decomp) |
| 9 | 1-naphthyl acetic acid | 69.50 | 7.34 | 6.00 | | | | 199 |
| | | 69.6 | 7.4 | 6.0 | | | | (decomp) |
| 10 | 4-pyridyl acetic acid | 54.88 | 6.49 | 8.73 | | | | 187 |
| | | 54.6 | 6.4 | 8.7 | | | | |
| 11 | 4-thianaphthene acetic acid | 64.18 | 7.44 | 7.13 | 9.02 | | 8.16 | >260 |
| | | 63.9 | 7.4 | 7.2 | 9.3 | | 8.0 | |

EXAMPLE 12

Tablets were prepared containing 200 mg of product of Example 1 and sufficient excipient of lactose, talc, starch and magnesium stearate for a final tablet weight of 800 mg.

EXAMPLE 13

An injectable solution (intra-muscular route) was prepared containing 50 mg of the product of Example 7 and sterile solvent for a volume of 5 ml.

PHARMACOLOGICAL STUDY

A. Bond to the opiated K receptor in vitro

Membrane residues were used preserved at $-30°$ C. (possibly for about 30 days) and prepared from guinea pigs brains. The residues were put into suspension in a buffer Tris pH 7.7 and 2 ml fractions were distributed in haemolysis tubes. $9^3H$ ethylketocyclazocine 1 nM was added as well as the test product. Theproduct was first tested at $5 \times 10^{-6}M$ (in triplicate). When the product tested displaced the radioactivity linked specifically to the receptor by more than 50%, it was tested again in a range of 7 doses to determine the dose which inhibits by 50% the radioactivity linked specifically to the receptor to determine the 50% inhibiting concentration. The non-specific link was determined by addition of a product called U-50488 H (Lahti et al 1982, Life Sci. Vol. 31, 2257) at $10^{-5}M$ in trilicate. It was incubated at $25°$ C. for 40 minutes and held in a water bath at $0°$ C. for 5 minutes, filtered under vacuum, rinsed with a buffer Tris pH 7.7 and the radioactivity was counted in the presence of a scintillating Trition.

The result is expressed directly as a 50% inhibiting concentration ($IC_{50}$), (the concentrationof the test product, expressed in nM, necessary to displace 50% of the specific radioactivity fixed on the receptor under study.

Results

The $IC_{50}$ found was 5.6 naomoles for the product of Example 1 and 5.3 nanomoles for the product of Example 7.

B. Anti-arrythmic action in the rat

Male rats weighing 300 to 350 g were tracheotomized after having been anaestetized intraperitoneally with 1.20 g/kg of urethane and were submitted to artificial respiration (40 to 50 insufflations of 3 ml/minute).

Needles were implanted sub-cutaneously to register the electrocardiogramm of the rats on the DII derivation signal.

The test products were administered intravenously and five minutes after the administration of the product, the jugular vein of the rats was prefused with 10 ug/nm from 0.2 ml of an aconitine solution and the time taken for disturbances of the cardiac rhythm to appear was noted. The results are expressed as a percentage of the protraction of the time taken for disturbances of the cardiac rhythm to appear as compared with controls and as a function of the dose of the product tested. The results appearing in the Table below show that the product of Example 2 was endowed with good antiarrythmic properties.

| Product of Example 2 | Dose mg/kg | Precentage of the protraction of time |
|---|---|---|
| | 10 | + 43% |
| | 5 | + 28% |
| | 2.5 | + 16% |

Various modifications of the products and methods of the invention may be made without departing from the spirit or scope thereof and it is to be understood that the invention is intended to be limited only as defined in the appended claims.

What we claim is:

1. A compound selected from the group consisting of all enantiomeric and diastereoisomeric forms of a decahydroquinoline of the formula

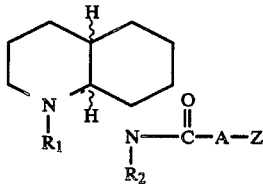

wherein $R_1$ is alkyl of 1 to 5 carbon atoms, $R_2$ is selected from the group consisting of hydrogen and alkyl of 1 to 5 carbon atoms, A is selected from the group consisting of $-(CH_2)_n$ and $-CH_2O-$, n is an integer from 1 to 5, Z is selected from the group consisting of phenyl, phenyl substituted with at least one member of the group consisting of alkyl and alkoxy of 1 to 5 carbon atoms, halogen, $-OH$, $-CF_3$, $-NO_2$ $-NH_2$ and mono and dialkylamino of 1 to 5 carbon atoms, naphthyl indenyl, and naphthyl and indenyl substituted with at least one member of the group consisting of alkyl and alkoxy of 1 to 5 carbon atoms, $-CF_3$, $-NO_2$, $-NH_2$, mono and dialkylamino of 1 to 5 carbon atoms and phenyl optionally substituted with one or more members of the group consisting of alkyl and alkoxy of 1 to 5 carbon atoms and halogen and their non-toxic, pharmaceutically acceptable acid addition salts and quaternary ammonium salts.

2. A compound of claim 1 wherein the juncture of the compounds of formula I is the cis form.

3. A compound of claim 1 wherein A is $-CH_2-$ or $-CH_2O-$.

4. A compound of claim 1 wherein $R_1$ is $CH_3-$ or $CH_3-CH_2-$ and Z is phenyl optionally substituted with 1 or 2 members of the group consisting of $CH_3-$, $CH_3-CH_2-$, $CH_3O-$, $CH_3-CH_2O-$, $Cl-$, $Br-$, $-CF_3$ and $-NO_2$.

5. A compound of claim 1, wherein $R_1$ is $CH_3-$ or $CH_3-CH_2-$, $R_2$ is hydrogen, methyl or ethyl and Z is naphthyl.

6. A compound of claim 1 selected from the group consisting of [4aRS(4aα,8α,8aα)](±) N-(decahydro-1-methyl-8-quinolinyl)-3,4-dichloro-N-methyl-benzene-acetamide and (4aα,8α,8aα) (±) N-(decahydro-1-methyl-8-quinolinyl)-[2-(3,4-dichlorophenoxy)]-N-methylacetamide and their non-toxic, pharmaceutically acceptable acid addition salts.

7. A central analgesic composition comprising a central analgesically effective amount of at least one compound of claim 1 and an inert pharmaceutical carrier.

8. A composition of claim 7 wherein the juncture of the compounds of formula I is the cis form.

9. A composition of claim 7 wherein in the compound of formula I, A is $-CH_2-$ or $-CH_2O-$.

10. A composition of claim 7 wherein, in the compound of formula I, $R_1$ is $CH_3-$ or $CH_3-CH_2-$ and Z is phenyl or phenyl substituted with 1 or 2 members of the group consisting of $CH_3-$, $CH_3-CH_2-$, $CH_3O-$, $CH_3-CH_2O-$, $Cl-$, $Br-$, $-CF_3$ and $-NO_2$.

11. A composition of claim 7, wherein in the compound of formula I, $R_1$ is $CH_3-$ or $CH_3-CH_2$, $R_2$ is hydrogen, methyl or ethyl and Z is naphthyl.

12. The composition of claim 7 wherein the active compound is [4aRS(4aα,8α,8aα)](±) N-(decahydro-1-methyl-8-quinolinyl)-3,4-dichloro-N-methyl-benzene-acetamide and (4aα,8α,8aα)(±) N-(decahydro-1-methyl-8-quinolinyl)-[2-(3,4-dichlorophenoxy)]-N-methylacetamide and their non-toxic, pharmaceutically acceptable acid addition salts.

13. A method of inducing central analgesic activity in warm-blooded animals comprising administering to warm-blooded animals a central analgesically effective amount of at least one compound of claim 1.

14. A method of claim 13 wherein the juncture of the compounds of formula I is the cis form.

15. A method of claim 13 wherein, in the compound of formula I, A is $-CH_2-$ or $-CH_2O-$.

16. A method of claim 13 wherein, in the compound in formula I, $R_1$ is $CH_3-$ or $CH_3-CH_2-$ and Z is a phenyl or phenyl substituted with 1 or 2 members of the group consisting of $CH_3-$, $CH_3-CH_2-$, $CH_3O-$, $CH_3-CH_2O-$, $Cl-$, $Br-$, $-CF_3$, and $-NO_2$.

17. A method of claim 13 wherein, in the compound of formula I, $R_1$ is $CH_3-$ or $CH_3-CH_2-$, $R_2$ is hydrogen, methyl or ethyl and Z is naphthyl.

18. The method of claim 13 wherein the active compound is [4aRS(4aα,8α,8aα)](±) N-(decahydro-1-methyl-8-quinolinyl)-3,4-dichloro-N-methyl-benzene-acetamide and (4aα,8α,8aα) (±) N-(decahydro-1-methyl-8-quinolinyl)-[2-(3,4-dichlorophenoxy)]-N-methylacetamide and their non-toxic, pharmaceutically acceptable acid addition salts.

* * * * *